United States Patent [19]

Chang et al.

[11] Patent Number: 5,685,860

[45] Date of Patent: Nov. 11, 1997

[54] SELF-CAPPING NEEDLE ASSEMBLY

[75] Inventors: Joseph J. Chang, Avon; Thomas Sloane, W. Redding, both of Conn.

[73] Assignee: Johnson & Johnson Medical, Inc., Arlington, Tex.

[21] Appl. No.: 483,549

[22] Filed: Jun. 7, 1995

[51] Int. Cl.⁶ ........................................................ A61M 1/00
[52] U.S. Cl. ............................................................ 604/192
[58] Field of Search ..................................... 604/198, 263, 604/192, 162, 187, 170; 53/409

[56] References Cited

U.S. PATENT DOCUMENTS

| | | |
|---|---|---|
| 3,134,380 | 5/1964 | Armao . |
| 4,790,828 | 12/1988 | Dombrowski . |
| 4,978,344 | 12/1990 | Dombrowski . |
| 4,994,041 | 2/1991 | Dombrowski . |
| 5,295,962 | 3/1994 | Crocker et al. . |
| 5,312,371 | 5/1994 | Dombrowski . |
| 5,368,566 | 11/1994 | Crocker . |
| 5,419,766 | 5/1995 | Chang et al. . |

*Primary Examiner*—Manuel Mendez

[57] ABSTRACT

An improved self-capping disposable needle assembly for use in combination with a skin puncture apparatus is provided. More specifically, an improved self-capping disposable needle assembly for use with a catheter which assembly contains a pleated sleeve made from any natural or synthetic fiber material is provided. The fiber materials employed as the pleated sleeve optionally may be treated with a suitable agent that provides the fiber material with a hydrophobic coating and prevents fluids such as blood from seeping therefrom.

15 Claims, 2 Drawing Sheets

SELF-CAPPING NEEDLE ASSEMBLY

FIELD OF THE INVENTION

The present invention provides an improved self-capping disposable needle assembly for use in combination with a skin puncture apparatus. More specifically, the present invention relates to an improved self-capping disposable needle assembly for use with a skin puncture apparatus such as a catheter assembly which contains a pleated sleeve made from any natural or synthetic fiber material. Moreover, the fiber material employed as the pleated sleeve may be braided, non-woven or woven and it, optionally, may be treated with a suitable agent that provides the fiber with a hydrophobic coating. Such a coating will prevent unwanted fluids such as blood from seeping through the fiber material during use.

BACKGROUND OF THE INVENTION

In today's health industry, there is an ongoing risk of exposure to infectious diseases such as human immunodeficiency virus (HIV) and other AIDS related viruses by health care workers who are continuously utilizing skin puncture apparatuses for injecting patients with medicaments. The term skin puncture apparatus is used herein to denote devices that are employed in the medical profession to pierce the skin of a patient. Such devices include IV catheter assemblies, intrascopic devices, hypodermic syringe assemblies, biopsy needles and sutures.

Because of this potential risk, disposable needles are considered by many individuals in the health care industry as being potentially infective and are accordingly handled with great care to avoid accidental contamination and/or injury. Moreover, a great deal of effort has gone into developing improved needle assemblies which are safer to handle and which prevent accidents from occurring.

One way of avoiding accidental contamination and/or injury is to advise health care workers to place disposable needles in puncture resistant containers. Although the use of puncture resistant containers represents a viable solution to the aforementioned problem, it is not a practical way since it presupposes that puncture resistant containers are available in all circumstances wherein contamination could occur.

In recent years it has become more convenient and safer to provide capping assemblies secured to each needle for immediate capping after use of the needle. One such capping assembly is disclosed in U.S. Pat. No. 3,134,380 to Armao. Specifically, this patent discloses a retractable needle guard which extends over the length of the needle assembly prior to use and is retracted as the needle is inserted into a patient. In the typical needle assembly of this kind, a shield which covers a significant portion of the needle shaft is provided at all times. Several drawbacks accordingly are associated with these types of needle assemblies. For example, these types of needle assemblies have less usable needle length when a conventional needle is adapted to the assembly; or they require a significantly longer needle shaft. Additionally, all the prior art needle assemblies of this type leave the distal tip of the needle exposed or capable of being exposed. Moreover, the tip of the needle is not locked in a completely enclosed guard. Therefore, needle assemblies as described in Armao may not fully protect health care workers from accidental contamination and/or injury.

More recent needle assemblies which overcome the aforementioned problems have been developed and are currently being used in health industries today. Such needle assemblies are described, for example, in U.S. Pat. Nos. 4,978,344 and 4,994,041, both to Dombrowski et al. Specifically, these patents to Dombrowski et al. disclose a needle assembly which includes a hub for connecting the assembly to a fluid conduit. The hub includes a passageway extending therethrough to receive a hollow needle in fluid communication therewith. The cap has a neutral position along the needle adjacent to the hub for exposing a length of the needle, and an extended position for capping the distal tip of the needle. The needle is disposed within a passageway of a catheter assembly whereby removal of the needle from the passageway of the catheter assembly moves the cap to the extended position, capping the distal tip as the cap is unseated from the catheter assembly.

A variation of the needle assemblies disclosed in the foregoing Dombrowski et al. patents is disclosed in U.S. Pat. No. 5,312,371 to Dombrowski et al. More specifically, this patent relates to a method for making a self-capping needle and catheter assembly which includes placing a needle hub and cap on a pin, with the pin extending through the passageway thereof. Two sheets of organic polymeric material are placed on the hub and the cap. The sleeve containing this organic polymeric material is then permanently stretched to a predetermined length. The cap, hub and organic polymeric sleeve are, according to this patent, placed on a needle and the cap is moved against the hub, folding the sleeve therebetween for reception of the catheter assembly.

In all of the foregoing Dombrowski et al. patents, the sleeves are made of an organic polymeric material which are pleated into bellows using elaborate and costly thermal processes. Moreover, in addition to being formed through complicated processing techniques, the plastic sleeves employed in the Dombrowski et al. patents have low tensile strength and high elongation. Thus, under some circumstances the sleeve may break resulting in possible contamination and/or injury of the person handling the needle.

In light of the prior art and the problems associated with those needle assemblies, research is ongoing to develop new and improved needle assemblies which are extremely safe to use and which overcome the drawbacks mentioned hereinabove.

SUMMARY OF THE INVENTION

The present invention is directed to an improved pleated sleeve material for use in self-capping needle assemblies which are adapted to receive a skin puncture apparatus connected thereto. The pleated sleeve materials employed in the present invention include braided, woven or non-woven fibers such as dacron, silk, cotton, polyester, rayon, wool, linen, satin and the like. Mixtures of these fibers are also contemplated herein. Such fibers have higher tensile strengths and lower elongation values than the pleated sleeves that are fabricated from organic polymeric materials. Because of these properties, the fiber sleeves of the instant invention are stronger than those heretofore known. Moreover, the fiber sleeves of the present invention, which include any natural or synthetic fiber, can be pleated or formed into bellows without the need for elaborate and expensive thermal processes such as those employed in the prior art.

As stated hereinabove, the term skin puncture apparatus is used herein to denote medical devices that are employed in the health industry to pierce the skin of a patient. Illustrative examples of such skin puncture apparatuses that may be employed in the instant invention include, but are not limited to, IV catheter assemblies, intrascopic devices, hypodermic syringe assemblies, biopsy needles, sutures and the like. Of these skin puncture apparatuses, catheters are particularly preferred.

In a highly preferred embodiment of the present invention, the fiber material is treated with a suitable agent that forms a pleated sleeve which contains a hydrophobic coating thereon. Such a coating prevents blood and/or fluids that are inside the sleeve from seeping through the fiber material. Specific types of agents that may be employed in the instant invention are fluorocarbon-based materials that have a low energy effect when applied to the natural or synthetic fibers.

DETAILED DESCRIPTION OF THE INVENTION

Figure 1:
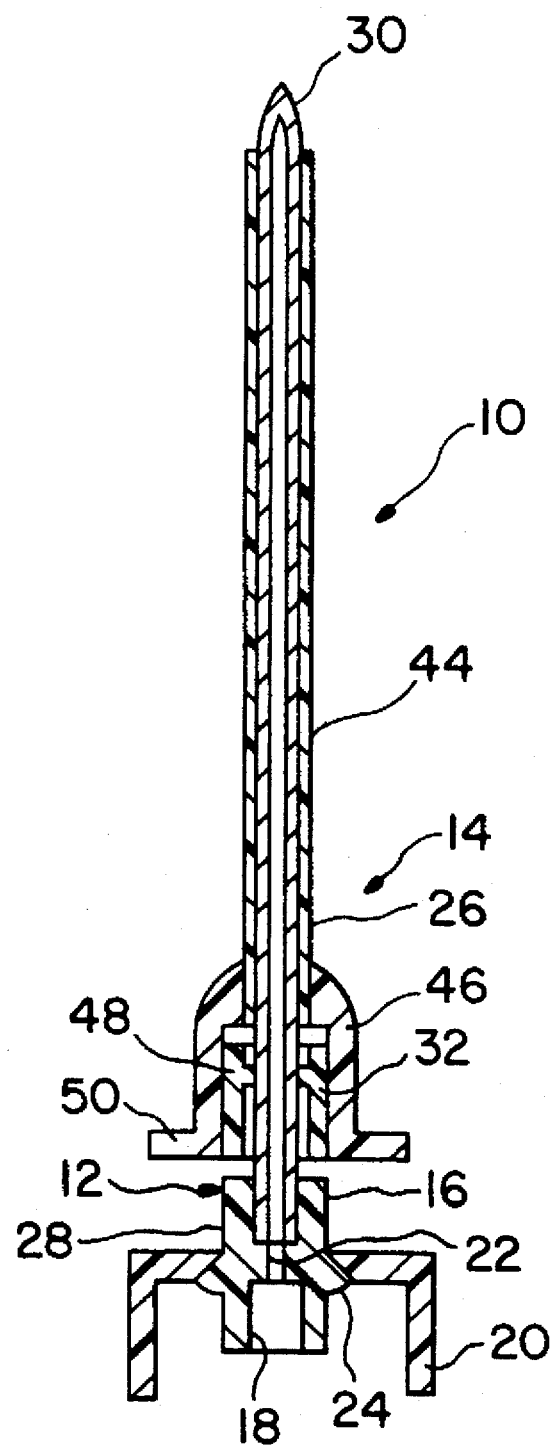
FIG. 1 is a longitudinal cross-sectional view of a needle assembly that may be employed in the present invention.

As stated above, the present invention provides an improved pleated sleeve material for use in self-capping disposable needle assemblies that are adapted for use with a skin puncture apparatus. Although a wide variety of needle assemblies and skin puncture apparatuses may be employed in the present invention, reference is made to the accompanying drawings which illustrate one type of needle assembly and catheter assembly that may be employed in the present invention.

It should be noted that the basic structure of both the needle assembly and catheter assembly described hereinbelow and as depicted in the accompanying drawings are well known to those skilled in this art. For example, such structures are disclosed in U.S. Pat. Nos. 4,790,828, 4,994,041 and 5,312,371 all to Dombrowski et al. It also emphasized that the sleeve materials of the present invention may be used in other needle assemblies and skin puncture apparatuses that are known to those skilled in this art.

In each of the figures, the needle assembly is indicated as 10. The needle assembly 10 of the instant invention includes a combination of a hypodermic needle assembly 12 and a catheter assembly 14. Other skin puncture apparatuses such as intrascopic devices, hypodermic syringe assemblies, biopsy needles and sutures may be used in place of catheter assembly 14.

Specifically, the hypodermic needle assembly 12 includes a hub portion 16 having an inner cup shaped surface 18 adapted to be connected to a syringe barrel 20. The hub 16 of the hypodermic needle assembly includes a passageway 22 extending therethrough. The hub 16 also includes a radially outwardly extending flange 24 which is employed in the present invention to secure hub 16 to syringe barrel 20 with an appropriate type of locking mechanism such as a luer-locking mechanism.

Needle assembly 10 further includes a hollow metallic needle 26 having a base 28 which is reversibly fitted into passageway 22 of hub 16. The hollow needle is in fluid communication with passageway 22 and it includes a distal tip 30 which is a sharp pointed beveled portion adapted for puncturing the skin of a patient. Such a distal tip is well known to those skilled in this art.

Figure 2:
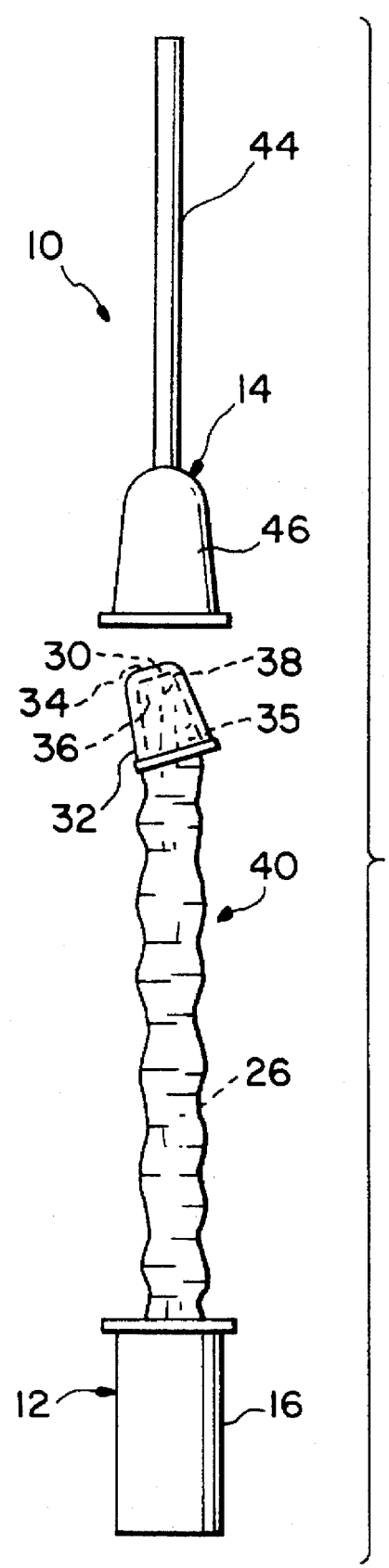
FIG. 2 is a side view of a catheter being completely removed from the needle assembly.

Needle assembly 10 also includes a cap 32 having a neutral position along needle 26 positioned near hub 16 for exposing the length of needle 26 as shown in FIG. 1. Cap 32 also has an extended position for capping distal tip 30 as shown in FIG. 2. Cap 32 includes a cap passageway 34 to allow passage of needle 26 therethrough and an inner surface 35 having at least one flange 36 extending therefrom and tapered towards hub 16. The flange 36 forms closed corners 38 defined by inner surface 35.

In the extend position which is shown in FIG. 2, flange 36 covers needle tip 30 and prevents the needle tip from re-entering passageway 34. The cap 32 contains an outer seating surface not shown in the accompanying drawings for receiving the catheter assembly 14.

Needle assembly 10 also includes a sleeve 40 for connecting cap 32 to hub 16. The sleeve 40 also serves to limit the extent cap 32 can be extended from hub 16. Cap 32 may extend from hub 16 to the full length of needle 26 and, when in combination with flange 36, it deflects the needle tip 30 into closed corners 38. The needle tip is thereafter locked under cap 32 when it is relocated to the extended position. When sleeve 40 is fully extended, flange 36 is in combination with sleeve 40, thus providing a sufficient means for locking cap 32 over distal tip 30 of needle 26.

Sleeve 40 employed in the present invention is in the form of an expandable pleated or bellow-shaped sleeve interconnecting hub 16 and cap 32 for perfecting a seal and closure about the full length of needle 26 when the cap is extended as shown in FIG. 2.

In accordance with the instant invention, the sleeve is made from any natural or synthetic fiber material. More specifically, the fiber materials that are employed in the present invention as the sleeve material may be braided, woven or non-woven fibers. Specific types of fiber materials that may be employed in the present invention as sleeve 40 include, but are not limited to, silk, cotton, rayon, linen, dacron, wool, satin, nylon, polyester and the like. Mixtures of the fiber materials are also contemplated in the present invention. Of these fibers, polyesters are particularly preferred as the sleeve material.

As stated above, when sleeve 40 is composed of a fiber material it will have a higher tensile strength and lower elongation value compared to plastic materials that are commonly employed in the prior art as the sleeve material. Because of the foregoing properties, the sleeve of the present invention is highly resistant to accidental breakage and it is easier to expand over needle 26.

Sleeve 40 is made by forming two sheets of fiber material about hub 16 and cap 32, sealing the edges thereof, and fastening it to hub 16 and cap 32. The sealing of the edges of the two fiber materials and the fastening to hub 16 and cap 32 are performed using conventional techniques that are well known to those skilled in this particular field.

In a highly preferred embodiment of the instant invention, the fiber material is coated with an agent which provides sleeve 40 with a hydrophobic coating. By forming a hydrophobic coating around sleeve 40, fluids inside the sleeve, such as blood, are prevented from seeping through the sleeve material. Suitable agents that may be used to provide sleeve 40 with a hydrophobic coating include fluorocarbon-based materials which have a low surface energy effect on the fiber material when applied thereto. Specific examples of such fluorocarbon-based materials include, but are not limited to, fluoromethane, fluoroethane, fluoropropane, fluoroethene, fluoropropene and the like. Mixtures of these fluorocarbon-based materials are also contemplated in the present invention.

The hydrophobic coating may be provided using conventional coating techniques that are well known to those skilled in the art. For example, the hydrophobic coating may be provided to the fiber material by lamination, direct calendaring, direct coating or transfer coating. The foregoing description provides a detailed account of the needle assembly 10 employed in the present invention.

The following provides a description of the catheter assembly 14 used in the present invention. As stated above other skin puncture apparatuses such as intrascopic devices, hypodermic syringe apparatuses, biopsy needles and sutures may be used instead of catheter assembly 14.

The catheter assembly 14 shown in FIG. 2 includes a shaft portion 44 which is disposed about the uncovered length of needle 26 and acts to expose distal tip 30. In this particularly position, distal tip 30 may initiate a puncture through a patient's skin and gain entry to the patient such that shaft portion 44 of the catheter 14 enters the patient. The catheter assembly 14 also contains a catheter hub 46 connected to shaft portion 44 and having an inner surface for releasable seating on the cap seating surface 48 whereby removal of needle 26 from shaft 44 moves cap 32 to the extended position, as hub 46 of the catheter assembly is unseated from the seating surface of cap 32. Distal tip 30 of needle 26 is concurrently capped as needle 26 is removed from the catheter assembly.

By adopting the above structure, a person administering the injection such as a nurse or doctor does not have to remove needle assembly 12 from catheter assembly 14, and then separately cap distal tip 30 of needle 26. This greatly reduces the probability of accidental contamination and/or injury. Instead, needle 26 is capped in a single motion. It should be noted that sleeve 40 of the present invention also maintains cap 32 locked against distal tip 30.

In accordance with the present invention, seating surface 48 provides an outer cylindrical or frustoconical surface for cap 32. The catheter hub 46 includes an inner complementing surface defining a seat in friction fit over seating surface 48 when cap 32 is in a neutral position. Other reversible methods of seating or connecting the seating surface are also contemplated in the present invention. The hub 46 also includes radially outwardly extending annular flange 50 which permits for a luer lock of the catheter.

In operation, catheter assembly 14 is seated over cap 32 and both are disposed adjacent to hub 16. After catherization, the hub portion 16 is moved away from the catheter 14 withdrawing needle 26 from the catheter and extending sleeve 40. The hub 16 depending on the particular use may or may not contain a hypodermic syringe assembly 20.

After cap 32 is fully extended so that flange 36 is covered by distal tip 30 in closed corners 38, the length of sleeve 40 acts to limit any further extension of cap 32, and flange 36 deflects distal tip 30 to prevent it from re-entering cap passageway 22 by moving it into closed corners 38 thereby irreversibly capping needle 26. As is illustrated in FIG. 2, upon further removal of needle assembly 10 from catheter assembly 14, cap 32 becomes unseated from catheter hub 46. When catherization is done in one single motion, the withdrawal of the remainder of the needle assembly from the catheter assembly 14 extends and covers cap 32 over distal tip 30 while simultaneously releasing the catheter therefrom.

Thus, the present invention provides a more efficient and safer means for catherizing a patient than heretofore known. Moreover, since sleeve 40 is made from a braided, woven or non-woven fiber, it has a higher tensile strength and lower elongation value than would a sleeve made of plastic material. Such properties result in a needle assembly which is more durable and less likely to break than those disclosed in the prior art. Furthermore, unlike plastic sleeves which require elaborate and expensive thermal processes for pleating, the sleeves of the present invention are pleated using conventional processes which are less expensive and not as elaborate as those required for pleating plastic sleeves.

While the present invention has been particularly shown and described with respect to preferred embodiments thereof, it will be understood by one skilled in the art that the foregoing and other changes in form and details may be made therein without departing from the spirit and scope of the instant invention.

What is claimed is:

1. A disposable needle assembly for use in combination with a skin puncture apparatus, said assembly comprising a needle assembly including a needle having a sharpened distal tip and a pleated hydrophobic sleeve surrounding said needle wherein said pleased sleeve is made from a natural or synthetic fiber material wherein the fiber material is braided, woven or non-woven.

2. The assembly of claim 1, wherein the fiber material is silk, cotton, rayon, linen, wool, satin, nylon, polyester or mixtures thereof.

3. The assembly of claim 2, wherein the fiber material is polyester.

4. The assembly of claim 3, wherein the fiber material is treated with an agent which is effective to provide a hydrophobic coating to said fiber.

5. The assembly of claim 4, wherein said agent is a fluorocarbon-based material which has a low surface energy effect when applied to said fiber material.

6. The assembly of claim 5, wherein the fluorocarbon-based material is fluoromethane, fluoroethane, fluoropropane, fluoroethene, fluoropropene or mixtures thereof.

7. The assembly of claim 1 wherein said needle assembly further comprises:
   a hub portion for connecting said needle assembly to a fluid conduit, said hub portion including a passageway extending therethrough;
   a hollow needle portion in fluid communication with said hub passageway, said needle portion having a distal tip relative to said hub portion;
   a cap including said pleated sleeve for connecting the hub portion to said cap and limiting the extent to which the cap can be extended from the hub portion, and locking means for locking said cap over said distal tip when said pleated sleeve is fully extended, said cap having a neutral position along said needle portion near said hub portion of said needle assembly for exposing a length of said needle portion, and an extended position for capping said distal tip.

8. The assembly of claim 7, wherein said skin puncture apparatus is a catheter assembly, an intrascopic device, a syringe needle apparatus, a biopsy needle or a suture.

9. The assembly of claim 8, wherein the skin puncture apparatus is a catheter assembly.

10. The assembly of claim 9 wherein said catheter assembly includes a passageway therethrough, a shaft portion disposed about said exposed length of said needle portion and exposing said distal tip, and a catheter hub for releasable seating on said cap whereby removal of said needle portion from said shaft portion moves said cap relative to said needle portion to said extended position capping said distal tip as said catheter hub is unseated from said cap.

11. The assembly of claim 10, where said cap further includes a releasable securing means for positively securing said cap with said catheter assembly as said needle portion is disposed within said passageway of said catheter assembly and releasing said cap from said catheter assembly when said cap is moved to said extended position whereby removal of said needle portion from said passageway of said catheter assembly moves said cap relative to said needle portion to said extended position capping said distal tip as said capping means is unseated from said catheter assembly.

12. A disposable needle assembly for use in combination with a skin puncture apparatus, said assembly comprising:

a catheter assembly including a passageway therethrough;

a hub portion for connecting said needle assembly to said catheter assembly, said hub portion including a passageway extending therethrough;

a hollow needle portion in fluid communication with said hub passageway, said needle portion having a distal tip relative to said hub portion;

a cap including (i) a pleated sleeve for connecting the hub portion to said cap and limiting the extent to which the cap can be extended from the hub portion, wherein said pleated sleeve is hydrophobic and composed of a natural or synthetic fiber material; (ii) locking means for locking said cap over said distal tip when said pleated sleeve is fully extended, said cap having a neutral position along said needle portion near said hub portion of said needle assembly for exposing a length of said needle portion and an extended position for capping said distal tip; and (iii) a releasable securing means for positively securing said cap with said catheter assembly as said needle portion is disposed within said passageway of said catheter assembly and releasing said cap from said catheter assembly when said cap is moved to said extended position whereby removal of said needle portion from said passageway of said catheter assembly moves said cap relative to said needle portion to said extended position capping said distal tip as said capping means is unseated from said catheter assembly.

13. The assembly of claim 12, wherein the fiber material is braided, woven or non-woven.

14. The assembly of claim 13, wherein the fiber material is silk, cotton, rayon, linen, wool, satin, nylon, polyester or mixtures thereof.

15. The assembly of claim 14, wherein the fiber material is polyester.

* * * * *